US00PP15528P2

(12) United States Plant Patent
Heims et al.

(10) Patent No.: US PP15,528 P2
(45) Date of Patent: Feb. 1, 2005

(54) ***TIARELLA* PLANT NAMED 'CANDY STRIPER'**

(50) Latin Name: ***Tiarella* spp.**
Varietal Denomination: Candy Striper

(75) Inventors: Daniel M. Heims, Portland, OR (US); Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 10 days.

(21) Appl. No.: 10/844,909

(22) Filed: May 12, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct cultivar of *Tiarella* plant characterized by its large size, upright habit and very large deeply palmately lobed leaves with a dark stripe down the veins.

1 Drawing Sheet

Botanical classification: *Tiarella* spp.
Variety denomination: 'Candy Striper'.

BACKGROUND OF THE INVENTION

The present invention relates to a new and distinct cultivar of a hardy herbaceous perennial of the genus *Tiarella,* and known by the cultivar name 'Candy Striper'. The genus *Tiarella* is a member of the family Saxifragaceae.

The new cultivar originated as a cross between unknown parents. This new *Tiarella* was one of many seedlings grown from select interspecific hybrids and species that were mass pollinated in the greenhouse in Canby, Oreg. From observation of the characteristics exhibited by the instant plant, it has *Tiarella cordifolia* and *T. wherryi* in its parentage.

SUMMARY OF THE INVENTION

This plant is characterized by the following:

1. Large size.
2. Mounding habit.
3. Large, palmately divided leaves with a dark stripe down each division.
4. Light pink flower buds and white flower color.
5. Excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year old *Tiarella* 'Candy Striper' in bloom grown in the ground in the garden in May in Canby, Oreg.

DETAILED PLANT DESCRIPTION

The following is a detailed description of the new *Tiarella* hybrid based on observations of two-year-old plants grown in the garden in shade in Canby, Oreg. The color descriptions are all based on The Royal Horticultural Society Colour Chart.

Botanical classification: *Tiarella* spp.
Variety denomination: 'Candy Striper'.
Plant:
- *Type.*—Herbaceous perennial.
- *Hardiness.*—USDA Zones 4 to 9.
- *Form.*—Mounding.
- *Size.*—55 cm wide and 28 cm. high.

Foliage:
- *Type.*—Simple.
- *Arrangement.*—Alternate, when visible on old stems.
- *Shape.*—Ovate.
- *Lobing.*—Varies. 7 to 9 lobes. Top three lobes are lanceolate and deeply cut. The terminal lobe is cut to the petiole. On spring leaves the terminal three lobes overlap while in the summer leaves they do not. The terminal lobe is the longest. The lobe sides are usually smooth on the bottom ⅓. In the summer the terminal lobe has 2–4 side lobes ⅔ down.
- *Margins.*—Crenate.
- *Venation.*—Palmate.
- *Apex.*—Mucronulate.
- *Base.*—Cordate.
- *Blade length.*—16 cm.
- *Blade width.*—13 cm.
- *Texture.*—Thin, rough.
- *Aspect.*—Matte.
- *Surface.*—Hispid top and bottom.
- *Petiole length.*—14 cm.
- *Petiole vestiture.*—Hirsute.
- *Petiole color.*—Grey red brown, Brown 200B.
- *Leaf color.*—Spring abaxial — Deep green, Green 137A, with a dark pattern along the veins, Greyed Purple 187A. Summer abaxial — Glossy. Green 137A with the dark pattern on the new leaves, Brown 200A, and fading with maturity. Adaxial — Yellow Green 146A.

Inflorescence:

*Type.*—Raceme.

*Flower number.*—50 per raceme.

*Bloom period.*—April to May with sporadic rebloom throughout the summer and fall.

*Peduncle.*—with 0 to 3 branches and 1 small divided leafy bract. Height — Grows to 45 cm. Width — 2 mm. at the widest point. Color — Brown 200A. Texture — Hispid.

*Pedicel.*—Length — 0.9 cm. Texture — Hispid. Color — Pink, Greyed Purple 182B.

*Lastingness.*—A raceme blooms for about 3 weeks.

Flower bud:

*Size.*—0.4 cm deep and 0.2 cm wide.

*Description.*—Ovoid, downfacing until open.

*Color.*—Pink, Greyed Purple 182D.

Flower:

*Type.*—Perfect, actinomorphic, sepals petaloid.

*Shape.*—Rotate.

*Flower size.*—1 cm wide and 5 mm deep including stamens and pistil.

*Petal number.*—5.

*Petal shape.*—Lanceolate with a clawed base.

*Petal size.*—4 to 5 mm long and 0.6 mm. wide.

*Petal color.*—White 155D.

*Calyx.*—5, petaloid, parted almost to the base, reflexed.

*Calyx color.*—White 155A.

*Sepal.*—5 in number, lanceolate, lobes 4 mm long and 1.5 mm wide.

*Stamens.*—10, conspicuously exerted.

*Filaments.*—White 155D, 0.6 cm long.

*Anthers undehisced.*—Red 37A.

*Pollen color.*—Greyed Orange 170A.

*Pistil.*—White 155A, 6 mm long.

*Fragrance.*—Sweet.

Fruit:

*Type.*—A one-celled capsule, beak-like, composed of two unequal parts.

*Size.*—0.7 cm long.

*Color.*—Brown 200C.

Seeds:

*Color.*—Black 202A.

*Shape.*—Minute, oval, 1 mm long.

*Fertility.*—Fertile.

Disease resistance: This new hybrid shows good mildew tolerance, the main problem for *Tiarella.*

COMPARISONS WITH SIMILAR *TIARELLA*

Compared with *Tiarella* 'Ninja' (U.S. Plant Pat. No. 11,168), *Tiarella* 'Candy Striper' has a much larger leaf.

Compared to *Tiarella* 'Black Snowflake' (U.S. Plant Pat. No. 13,684) the new cultivar has larger leaves with fewer, broader lobes, a lighter pattern, and a more upright habit Compared to *Tiarella* 'Iron Butterfly' (U.S. Plant Pat. No. 12,396), the new cultivar has a much larger leaf and white rather than pink flowers. They share a similar leaf shape.

I claim:

1. A new and distinct cultivar of *Tiarella* plant characterized by its large size, upright habit and very large deeply palmately lobed leaves with a dark stripe down the veins.

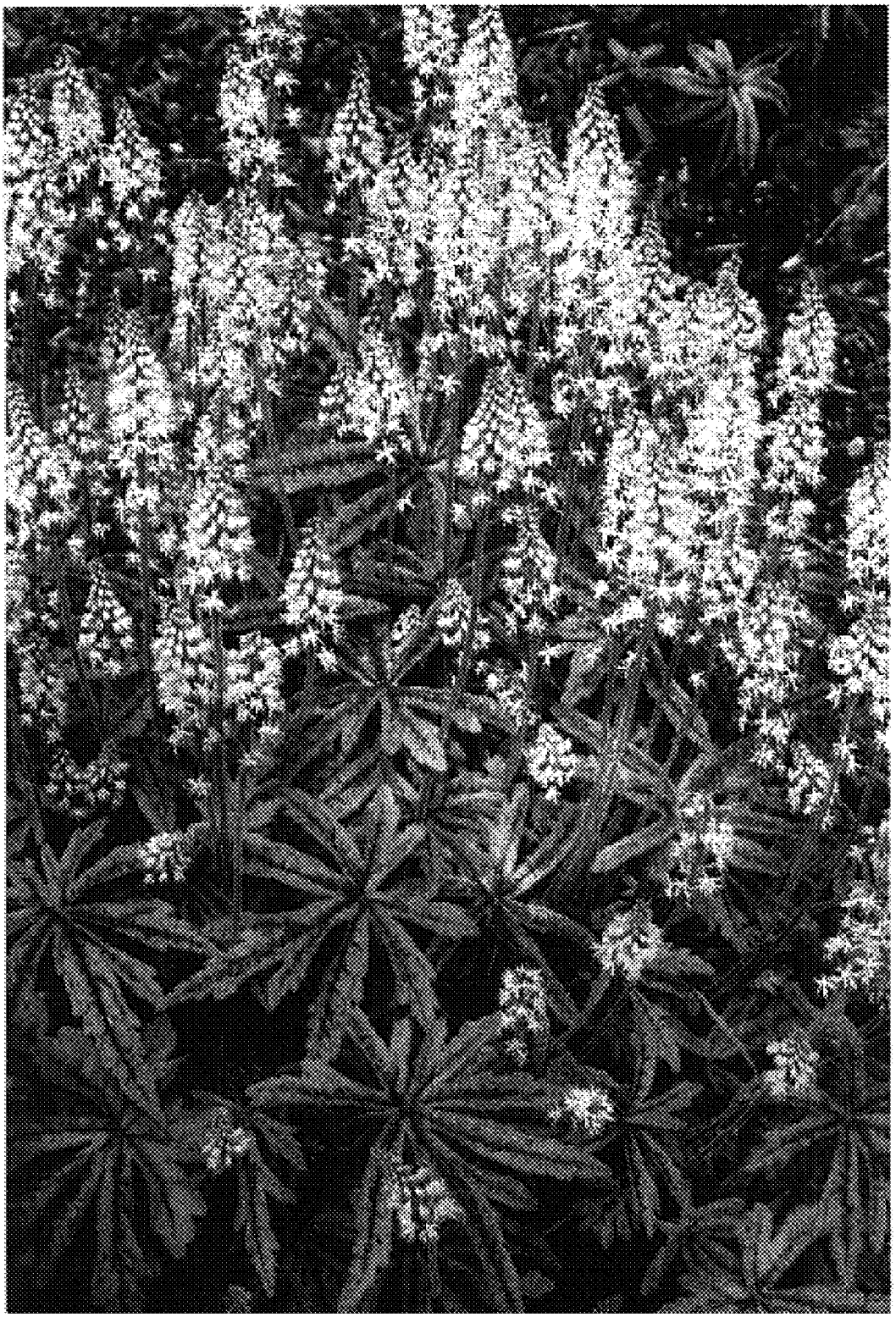

* * * * *